United States Patent
Reeves et al.

(12) 
(10) Patent No.: US 6,265,346 B1
(45) Date of Patent: *Jul. 24, 2001

(54) METHOD FOR PRESERVING FRESH CUT FLOWERS AND THE PRESERVED FLOWERS PRODUCED THEREFROM

(75) Inventors: Scott M. Reeves; Laura C. Reeves, both of Phoenix, AZ (US)

(73) Assignee: Laura Sullivan Reeves, Phoenix, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/013,277

(22) Filed: Jan. 26, 1998

(51) Int. Cl.⁷ ....................................... A01N 3/02
(52) U.S. Cl. ............................................... 504/114
(58) Field of Search ............................................ 504/114

(56) References Cited

U.S. PATENT DOCUMENTS

| | | | |
|---|---|---|---|
| 116,375 | * | 6/1871 | Vining .................................. 504/114 |
| 1,779,299 | * | 10/1930 | Valentine ............................. 504/114 |
| 3,865,569 | * | 2/1975 | Parups et al. ............................ 71/68 |
| 3,929,448 | * | 12/1975 | Brantley ............................... 504/114 |
| 4,061,490 | * | 12/1977 | Yukinaga et al. ........................ 71/68 |
| 4,272,571 | * | 6/1981 | Romero-Sierra et al. ............. 428/24 |
| 5,580,840 | * | 12/1996 | Harms et al. ......................... 504/115 |

OTHER PUBLICATIONS

Creekmore, Betsey B. Making Gifts from Oddments and Outdoor Materials. NY:Hearthside Pr. Inc. p. 167–169, 1970.*

* cited by examiner

*Primary Examiner*—S. Mark Clardy
(74) *Attorney, Agent, or Firm*—Laura Sullivan Reeves

(57) ABSTRACT

A method for preserving a fresh flower includes coating the flower with beeswax and applying a protective sealant of natural lacquer over the beeswax. Dye and/or fragrance may be added to the beeswax. The preserved flower produced therefrom includes a first beeswax coating and a second protective sealant coating. The fresh flowers so preserved substantially retain their original appearance and fragrance.

20 Claims, No Drawings

METHOD FOR PRESERVING FRESH CUT FLOWERS AND THE PRESERVED FLOWERS PRODUCED THEREFROM

FIELD OF THE INVENTION

This invention relates generally to flowers and more specifically to a method for preserving fresh cut flowers and the preserved flowers produced therefrom.

BACKGROUND OF THE INVENTION

Showy flowers are beloved by many for their appearance by adding color, drama, and beauty to their surroundings. Showy flowers can brighten a room, a garden, even a mood and provide changing interest throughout the year. In addition, a flower's fragrance can be as memorable as its appearance; the scent of a particular blossom can evoke a past experience. For these reasons, flowers have been used since time immemorial in various settings. Flowers have been used ceremonially such as in funerals, weddings, and in sick visits and as part of romantic rituals. Flowers, usually cut, appear in centerpieces, bouquets, gifts, etc. Some flowers, particularly exotics and tropicals, are very desirable yet very expensive and usually available only seasonally. Unfortunately, a flower's beauty and fragrance are short-lived, the flower often dying only a few days after being cut from the plant.

Attempts have been made to recreate or retain the beauty of flowers with artificial flowers and with fresh flowers. Artificial flowers, typically made from plastic or silk, do not successfully capture the beauty of a fresh flower. Fresh flowers may be preserved chemically (See egs., U.S. Pat. Nos. 3,865,569; 4,061,490; 4,272,571; and 5,580,840) or by drying, but both methods drastically alter the appearance of the flower and increase its frailty. Moreover, dried flowers do not last in areas of high humidity. Even in ideal conditions, dried flowers do not last unless placed under glass.

Paraffin wax has also been used as a fresh flower preservative. (Making Gifts from Oddments and Outdoor Materials by Betsey B. Creekmore (Hearthside Press Inc. 1970)). The natural colors of fresh flowers are dimmed by a coating of paraffin wax and when exposed to the air, the paraffin wax-coated flowers lose their color, eventually turning the flower dark brown in color. Fresh flowers preserved with paraffin therefore last only for a short period of time, typically about a week. Moreover, preserving fresh flowers with paraffin requires extra caution since paraffin is a petroleum by-product, melts at 100 degrees Fahrenheit, is highly flammable, explosive and toxic and thus poses strict requirements for handling. Paraffin is also dangerous when ingested and thus no paraffin-coated flower is edible.

Accordingly, there has been a need for a novel method to preserve fresh cut flowers and the preserved flowers produced therefrom which substantially retain the appearance, size, shape, color and fragrance of the uncut fresh flower. There is a still further need for a method to preserve fresh cut flowers such that seasonal flowers can be preserved and thus available year-round to enjoy. Additionally, a method is needed which is all natural producing preserved flowers that can be used on food, such as a cake decoration and could be ingested assuming the flower was edible. The present invention fulfills these needs and provides other related advantages.

SUMMARY OF THE INVENTION

The present invention resides in an improved method for preserving freshly cut flowers and the preserved flowers produced therefrom. The method comprises the steps of, generally, coating a freshly cut flower with beeswax, and providing a sealant for protecting the beeswax-coated flower against primarily discoloration. The preserved flower produced therefrom comprises, generally, a flower having a first beeswax coating and a second sealant coating thereon.

In a preferred form of the invention, the method produces preserved flowers that substantially retain the appearance and fragrance of the freshly cut flower. The coating step includes dipping a rehydrated and clean freshly cut flower into melted beeswax to which dye and fragrance have been optionally added, cooling the beeswax coated flower and curing the beeswax coated flower to remove moisture to avoid mildew, rot and discoloration. Curing includes removing the beeswax-coated flower from a stem supporting the flower and ventilating the flower.

The sealing step includes applying a protective sealant to the beeswax coated flower. The protective sealant is preferably a natural lacquer.

Other features and advantages of the present invention will become more apparent from the following more detailed description.

DETAILED DESCRIPTION OF THE PREFERRED EMBODIMENTS

The present invention is concerned with a method for preserving a fresh flower and the preserved flower produced therefrom. The method of preserving the fresh flower comprises, generally, coating a fresh flower with melted beeswax and sealing the beeswax-coated flower with a protective sealant. A dye and/or a fragrance may be added to the melted beeswax.

In the method of the invention, a stem supporting the fresh flower is freshly cut, leaving about six to about eight inches with the flower. The flower is then rehydrated by being placed in cool fresh water and in a refrigerator for about three to about twelve hours. After rehydration, the flower is cleaned by removing any excess leaves and petals, if any, that are damaged.

The fresh flowers should preferably be no more than 24 hours off the plant when the fresh cut to the stem 18 is made. Exemplary flowers that may be preserved by the present invention include roses, tulips, peonies, daisies, pom poms, asters, geraniums, lavender, hydrangea, lizianthus and most wild flowers. The flowers to be preserved should preferably have petals with a low moisture content. To coat the flower, the rehydrated and cleaned flower is lowered into and then quickly raised from a container of melted beeswax to which dye and/or fragrance have been optionally added while holding onto the stem and rotating the upside down flower in a spinning motion. The flower should be submerged in the melted beeswax for no longer than about two seconds, preferably about one second. Once raised from the melted beeswax, the upside down flower should continue to be spun for about 15 to about 30 seconds after which the flower should be turned upright and spun for about an additional 15 to about 30 seconds.

The beeswax is preferably heated to about 150 to about 160 degrees Fahrenheit. The beeswax should be slowly melted such as in a double boiler, the container surrounded by water so as not to burn or scorch the beeswax. Any conventional heating means for melting the beeswax and heating the water may be used. The waxing temperature varies from flower to flower, gauged by the thickness and durability of the petals, if any. The optimal beeswax temperature for preserving roses seems to be about 157 degrees Fahrenheit.

The beeswax is an all natural wax, made from the honey bee, nontoxic and ingestible. The beeswax that is preferably used is artist's grade which is substantially pure and strained repeatedly until all the honey is removed, leaving a creamy white beeswax. Preferably, no bleach or preservatives are added to the beeswax. Beeswax melts at about 150 to about 158 degrees Fahrenheit, and is not flammable or explosive.

The dye may be added to the melted beeswax. The dye is preferably translucent. This enables the beeswax coat to be substantially translucent, keeping the color of the flower as close to natural as possible. If dye is used, it is preferably made to match the flower color, i.e. pink dye for pink flowers, red dye for red flowers, etc. If all flowers were coated in beeswax without dye, one would notice a white coating over a red, purple or other colored flower. The dye substantially prevents an unnatural waxy coating to show. The dye is also preferably nontoxic and ingestible for edible flowers.

The fragrance may also be added to the melted beeswax. The fragrance is preferably concentrated. The fragrance bonds with the beeswax and is held in a suspended state for a substantial length of time. When preserving a rose, for example, rose fragrance would preferably be added. The fragrance is also preferably nontoxic and ingestible for edible flowers.

After coating the flower with beeswax, the flower is rapidly cooled by immediately placing it in front of a fan on high speed until an opaque shell forms over the beeswaxed-coated flower. Once the shell forms, the flower should be further cooled for about one to about two hours in a refrigerated area with a temperature range of about 40 to about 45 degrees Fahrenheit.

After cooling the flower, the flower is then cured to remove any excess moisture to avoid mold, rot and discoloration. There is substantially no loss in the size or shape of the flower with curing. The beeswax-coated flower is removed from the stem including a receptacle portion thereof and any associated foliage such as the leaves. In addition, excess cavity petals are removed. The stem, artificial or otherwise, may be reattached later. The beeswax-coated flower is placed on a ventilated surface in a room maintained at a temperature of about 72 to about 78 degrees Fahrenheit with strategically-placed fans for constant air flow. The flower should be rotated daily. Every flower cures at a different rate depending on size, denseness and moisture level in the petal. The average curing time is about seven to about ten days. As examples only, roses are cured when the hollow cavity of the rose feels dry and crunchy to the touch. Tulips, daisies, pom poms are cured when a stem nub is dry and hard.

After curing, the protective sealant is then applied over the beeswax-coated flower. The protective sealant is preferably a natural lacquer which is nontoxic and ingestible. Of course, acrylic could also be used. The sealant substantially prevents a white coating which beeswax naturally develops over time. The sealant also raises the melting temperature of the beeswax, which is important as high temperatures may be reached during shipping. The natural lacquer is preferably applied via an HVLP spray dispenser over the flower and allowed to dry. The method of the invention takes approximately 10 days to two weeks to complete.

The method of the invention produces a preserved flower having a first coating of the beeswax and a second coating of the protective sealant. If necessary, an artificial stem may be constructed, for example, from wire and twigs and attached to the beeswax-coated flower with hot glue to produce the flower and supporting stem. The preserved flower can be arranged in, for example, a bouquet or centerpiece or if the fresh flower was edible and the sealant, dye and fragrance, if any, nontoxic and ingestible, used on food.

From the foregoing it is to be appreciated that a gardener can now preserve the beauty and fragrance of his or her flowers for many years in their fresh, open state. Their size, shape, color and fragrance are retained. Brides can now marry with a fresh looking bouquet that can perhaps be kept a lifetime without placing under glass. Flowers can be preserved along with their memories.

Although a particular embodiment of the invention has been described in detail for purposes of illustration, various modifications may be made without departing from the spirit and scope of the invention. Accordingly, the invention is not to be limited, except as by the appended claims.

We claim:

1. A method of preserving a flower comprising the step of:
   coating the flower with beeswax to produce a beeswax-coated flower.

2. The method of claim 1 further including the step of providing a sealant for protecting the beeswax-coated flower.

3. The method of claim 1 further including the step of melting the beeswax at a temperature of about 150 to about 160 degrees Fahrenheit.

4. The method of claim 3 further including the step of adding a dye to the melted beeswax.

5. The method of claim 4 wherein the dye includes a translucent dye.

6. The method of claim 3 further including the step of adding a fragrance to the melted beeswax.

7. The method of claim 3 wherein the step of coating the flower further comprises lowering the flower into the melted beeswax for no more than two seconds, then raising the flower from the beeswax while holding onto a stem supporting the flower and rotating the upside down flower in a spinning motion for about 15 to about 30 seconds after which the flower should be turned upright and spun for an additional about 15 to about 30 seconds.

8. The method of claim 7 wherein the step of coating the flower further comprises lowering the flower in the melted beeswax for about one second.

9. A method of preserving a freshly cut flower comprising the steps of:
   Rehydrating the freshly cut flower;
   Coating the freshly cut flower with melted beeswax to which dye and fragrance have been optionally added to produce a beeswax coated flower;
   Cooling the beeswax coated flower;
   Curing the beeswax coated flower; and
   Applying a protective sealant to the beeswax coated flower.

10. The method of claim 9 wherein the flower is freshly cut by cutting a stem supporting the flower, leaving about six to about eight inches of the stem with the flower.

11. The method of claim 9 wherein the step of rehydrating the freshly cut flower comprises placing it in cool fresh water and in a refrigerator for about three to about twelve hours.

12. The method of claim 9 wherein the step of curing comprises ventilating the beeswax coated flower.

13. The method of claim 12 wherein ventilating includes placing the beeswax coated flower on a ventilated surface in a room maintained at a temperature of about 72 to about 78 degrees Fahrenheit and substantially constant air flow.

14. The method of claim 12 wherein the step of curing further includes the step of removing the beeswax coated flower from the stem.

15. The method of claim 9 wherein the temperature of the melted beeswax is from about 150 degrees Fahrenheit to about 160 degrees Fahrenheit.

16. The method of claim 15 wherein the flower is a rose and the temperature of the melted beeswax is about 157 degrees Fahrenheit.

17. The method of claim 9 wherein the dye comprises a translucent dye.

18. The method of claim 9 wherein the step of cooling the beeswax coated flower includes placing the beeswax coated flower in front of a fan on high speed and then refrigerating the beeswax coated flower for about one to about two hours at a temperature range of about 40 to about 45 degrees Fahrenheit.

19. A preserved flower comprising in combination:
- a first coating of beeswax and optionally, a dye and/or fragrance; and
- a second coating of a protective sealant.

20. The preserved flower of claim 19 wherein the preserved flower is edible.

* * * * *